United States Patent
Sugai et al.

(10) Patent No.: US 6,496,255 B2
(45) Date of Patent: Dec. 17, 2002

(54) MEASUREMENT OF CRYSTAL FACE ORIENTATION

(75) Inventors: Kazumi Sugai; Belgacem Haba; Yukio Morishige, all of Tokyo (JP)

(73) Assignee: NEC Corporation (JP)

( * ) Notice: Subject to any disclaimer, the term of this patent is extended or adjusted under 35 U.S.C. 154(b) by 16 days.

(21) Appl. No.: 09/923,143

(22) Filed: Aug. 6, 2001

(65) Prior Publication Data

US 2002/0005952 A1 Jan. 17, 2002

Related U.S. Application Data

(62) Division of application No. 08/824,384, filed on Mar. 26, 1997.

(30) Foreign Application Priority Data

Mar. 26, 1996 (JP) .............................................. 8-69879

(51) Int. Cl.[7] .............................................. G01N 21/00
(52) U.S. Cl. ........................ 356/237.2; 356/31; 356/30
(58) Field of Search ........................ 356/237.1, 237.2, 356/237.3, 237.4, 237.5, 237.6, 30, 31, 369, 600; 438/14, 973, 733; 148/DIG. 115; 250/559.42, 559.45

(56) References Cited

U.S. PATENT DOCUMENTS

| 4,958,373 A | * | 9/1990 | Usami et al. ................... 382/8 |
| 4,995,063 A | * | 2/1991 | Enoki et al. ................... 378/70 |
| 5,633,711 A | * | 5/1997 | Nelson et al. ............... 356/318 |

FOREIGN PATENT DOCUMENTS

| DE | 19725535 | * | 6/1997 |
| JP | 402271241 | * | 11/1990 |
| JP | 4-198845 | * | 7/1992 |
| JP | 409222391 | * | 8/1997 |

* cited by examiner

Primary Examiner—Hoa Q. Pham
(74) Attorney, Agent, or Firm—Dickstein, Shapiro, Morin & Oshinsky, LLP.

(57) ABSTRACT

A sample is rotated about an axis perpendicular to a surface of the sample in predetermined angular steps. The surface of the sample is irradiated with linearly polarized light, and a reflected intensity of light reflected from the surface of the sample is detected in each angular step. Based on a rotational angle dependency of the reflected intensity, the crystal face orientation of the sample is determined. To improve signal-to-noise ratio, the crystal lattice of the sample is excited. Further, the surface of the sample is irradiated with a plurality of linearly polarized light beams to obtain a plurality of reflected intensities.

46 Claims, 11 Drawing Sheets

MEASUREMENT OF CRYSTAL FACE ORIENTATION

CROSS REFERENCE TO RELATED APPLICATION

This is a divisional of U.S. patent application Ser. No. 08/824,384, filed Mar. 26, 1997 in the name of Kazumi SUGAI et al., and entitled "Measurement of Crystal Face Orientation".

BACKGROUND OF THE INVENTION

1. Field of the invention

The present invention relates to measurement of a crystal face orientation, and more particularly to a method and an apparatus of measuring the crystal face orientation of a crystal material.

2. Description of the Prior Art

A semiconductor crystal of, for example, Group IV semiconductor such as silicon (Si) or compound semiconductor such as gallium arsenide (GaAs) and gallium phosphide (GaP), is cut out in the form of a wafer as a semiconductor device substrate which is commercially available. There has been known an X-ray diffraction method which obtains the information of interplanar spacing of a bulk crystal to measure the surface orientation.

According to another method described in Japanese Patent Unexamined Publication No. 58-210546, a crystal orientation is obtained from the rotational angle dependency of the intensity of Raman light that emerges from the crystal face.

SUMMARY OF THE INVENTION

The first conventional method above mentioned, however, has the disadvantage that the cost of measurement of crystal face orientation becomes increased, because it requires a large, expensive X-ray apparatus and also requires a safety countermeasure for X rays. The second method using the rotational angle dependency of the intensity of Raman light also has the disadvantage that high-precise measurements cannot tee achieved because of the week signal intensity of Raman light. In order to overcome the aforementioned disadvantages, we would like to propose a novel measuring method and apparatus.

An object of the present invention is to provide a method and apparatus which can precisely measure a crystal face orientation with reduced amount of hardware and cost.

Another object of the present invention is to provide a method and apparatus which can improve the signal-to-noise ratio to achieve the precise measurement of a crystal face orientation.

First, a description will be made of a method for obtaining a crystal face orientation from the angle dependency of the intensity of the second harmonic. When the surface of the crystal is irradiated with light of a certain wavelength, non-linear polarization will be induced and thereby light with a wavelength of half that of the incident light, called a second harmonic, will be emitted. The magnitude of polarization varies according to the direction of atom bonding within the crystal. Therefore, if linearly polarized light is employed as incident light, the intensity of emitted light will change in accordance with the arrangement of atoms within the crystal. Thus, it is possible to know a crystal face orientation by monitoring a change in the intensity of the light emitted from the surface of the crystal.

According to the present invention, a crystal face orientation is measured based on the angle dependency of the intensity of reflected light. The wavelength dependency of the reflectance coefficient of a crystal in the ultraviolet range exhibits a peak which reflects the energy band structure of the crystal. Since the energy band structure depends upon a crystal axis, the reflectance coefficient of incident light near the peak depends upon a relative angle between the direction of polarization of incident light and a crystal axis. Therefore, by irradiating a crystal face with light having a photon energy which corresponds to the specific transition energy of the crystal and also detecting the rotational angle dependency of the reflectance coefficient within the crystal plane, the crystal face orientation can be obtained.

However, since the reflected light from a crystal is very weak, it is very difficult to sufficiently measure a change in the intensify of the reflected light as it is. When a crystal is in room temperature, the lattice momentum is small. When the lattice momentum is near zero, the difference of the bandgap with respect to the crystallographic axis is small and therefore the difference of the reflectance coefficient with respect to the crystallographic axis is also small. For this reason, even if the reflectance coefficient were rotated within a crystal face while detecting the rotational dependency, the dependency would be too small to perform high precision measurements.

Therefore, we employ a means of increasing the signal-to-noise ratio. According to a first aspect of the present invention, a sample is rotated about an axis perpendicular to a surface of the sample in predetermined angular steps and a crystal lattice of the sample is excited or stimulated. Irradiating the surface of the sample with linearly polarized light, a reflected intensity of light reflected from the surface of the sample is detected in each angular step. Based on a rotational angle dependency of the reflected intensity, the crystalface orientation of the sample is determined.

Exciting the lattice momentum of the sample increases a change of the reflectance coefficient with respect to the crystallographic axis. For example, by heating or irradiating the sample with light or ultrasonic waves, it becomes possible to render the lattice momentum larger, and a crystal face orientation can be precisely measured.

We employ another means of increasing the signal-to-noise ratio. According to a second aspect of the present invention, the surface of the sample is irradiated with a plurality of linearly polarized light beams in each angular step. A plurality of positions on the surface of the sample may be irradiated with the linearly polarized light beams, respectively, the linearly polarized light beams being generated from a single linearly polarized light beam. The linearly polarized light beams may be formed by irradiating the surface of the sample with a single linearly polarized light beam a plurality of times in the same direction in each angular step. The means of exciting the crystal lattice of the sample may be combined to further improve the signal-to-noise ratio.

We employ still another means of increasing the signal-to-noise ratio. According to a third aspect of the present invention, a first linearly polarized light beam and a second linearly polarized light beam are generated from a single linearly polarized light beam. The surface of the sample is irradiated with the first linearly polarized light beam. A reflected intensity of light reflected from the surface of the sample and an intensity of the second linearly polarized light beam are detected in each angular step. The crystal face orientation of the sample is determined based on a rotational angle dependency of the reflected intensity adjusted by the intensity of the second linearly polarized light beam. The means of exciting the crystal lattice of the sample may be combined to further improve the signal-to-noise ratio.

We employ further still another means of increasing the signal-to-noise ratio. According to a fourth aspect of the present invention, the surface of the sample is irradiated with a first linearly polarized light beam and a second linearly polarized light beam in first and second directions, respectively, the first and second linearly polarized light beams having the same wavelength and the same direction of polarization. A first reflected intensity of light reflected in the first direction from the surface of the sample is detected in each angular step, and a second reflected intensity of light reflected in the second direction from the surface of the sample is also detected in each angular step. The crystal face orientation of the sample is determined based on a rotational angle dependency obtained from the first and second reflected intensities. The means of exciting the crystal lattice of the sample may be combined to further improve the signal-to-noise ratio.

According to the present invention, as previously described, it becomes possible to measure a crystal orientation with an improved signal-to-noise ratio and a high degree of accuracy using a structurally simple apparatus.

BRIEF DESCRIPTION OF THE DRAWINGS

The present invention will be described in further detail with reference to the accompanying drawings, in which.

DESCRIPTION OF THE PREFERRED EMBODIMENTS

FIRST EMBODIMENT

Figure 1:
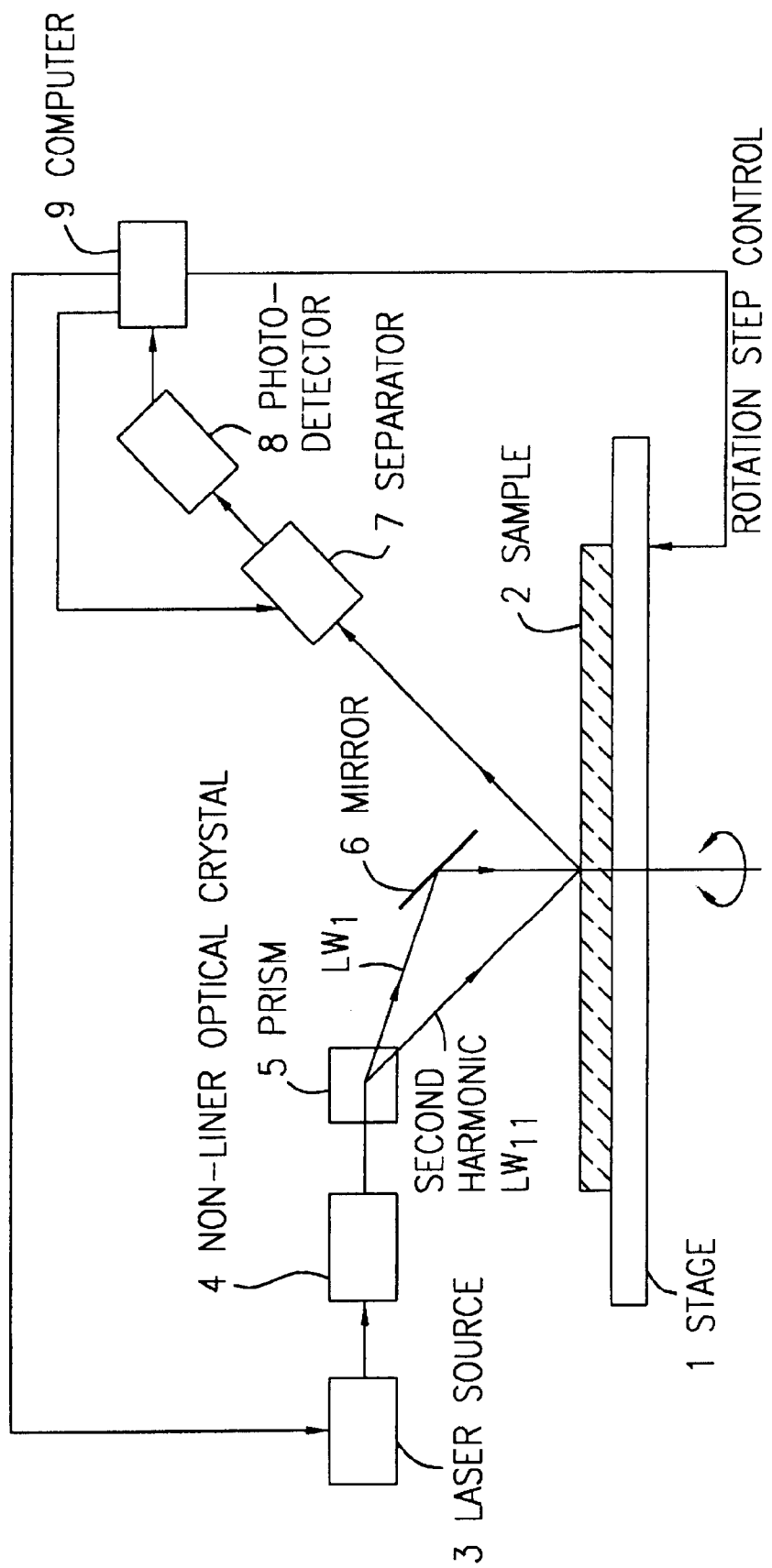
FIG. 1 is a schematic view showing an apparatus for measuring a crystal face orientation according to a first embodiment of the present invention.

Referring to FIG. 1, there is shown a measuring apparatus of a crystal face orientation according to a first embodiment of the present invention. A stage 1 is capable of rotating about the vertical axis in controlled angular steps. A sample 2 such as a crystal semiconductor is placed on the stage 1 and is irradiated with a fundamental $LW_F$ and a second harmonic $LW_H$ which are produced from a laser beam generated by a laser source 3. A non-linear optical crystal 4 produces the second harmonic from the laser beam and a prism 5 divides the output light of the non-linear optical crystal 4 into the fundamental $LW_F$ and the second harmonic $LW_H$. The fundamental $LW_F$ is reflected by a mirror 6 to be directed normal to the surface of the sample 2. The reflected second harmonic $LW_H$ from the sample 2 passes through a separator 7 before the intensity of the reflected light is detected by a photodetector 8.

A computer 9 includes a processor, a program memory, a data memory and other necessary devices which are not shown in this figure. The computer 9 stores data of the intensity of the reflected light at each rotation angle while rotating the stage 1 in predetermined angular steps. Based on the stored data, the computer 9 calculates the peak of the intensity to determine the crystal face orientation of the sample 2.

More specifically, a germanium (Ge) substrate with (111) plane is placed on the stage 1 as the sample 2. A pulse oscillation Nd:YAG laser of wavelength 1064 nm is employed as the laser source 3, and the output light of the laser source 3 is transmitted through the non-linear optical crystal 4 to generate a second harmonic. The generated second harmonic is split into the fundamental $LE_F$ and the second harmonic $LW_H$ by the prism 5. At this time, the fundamental $LE_F$ may be unpolarized light, and the second harmonic $LE_H$ may be polarized by a polarizer into p-polarized. light whose polarization plane is parallel to the incident plane of the second harmonic $LE_H$.

The fundamental $LE_F$ transmitted through the prism 5 is reflected by the mirror 6 and is incident on the surface of the sample 2 in a vertical direction. Also, the second harmonic $LW_H$ is incident on the surface of the sample 2 at a certain angle relative to the surface. The reflected light of the second harmonic $LW_H$ from the sample 2 is transmitted through the separator 7 which removes interfering light therefrom, and the intensity of the reflected light is detected by the photodetector 8 and is stored onto the data memory of the computer 9.

Subsequently, the stage 1 is rotated by an angle of 0.1°, and in the same procedure as the aforementioned, the intensity of the second harmonic $LW_H$ is stored. By repeating this process, the intensities of the second harmonic $LW_H$ are stored over 360°. At this time, the reflectance coefficient becomes high only at the angle where the direction of polarization of the second harmonic matches the <111>-axis. This phenomenon is explainable as follows.

Figure 2:
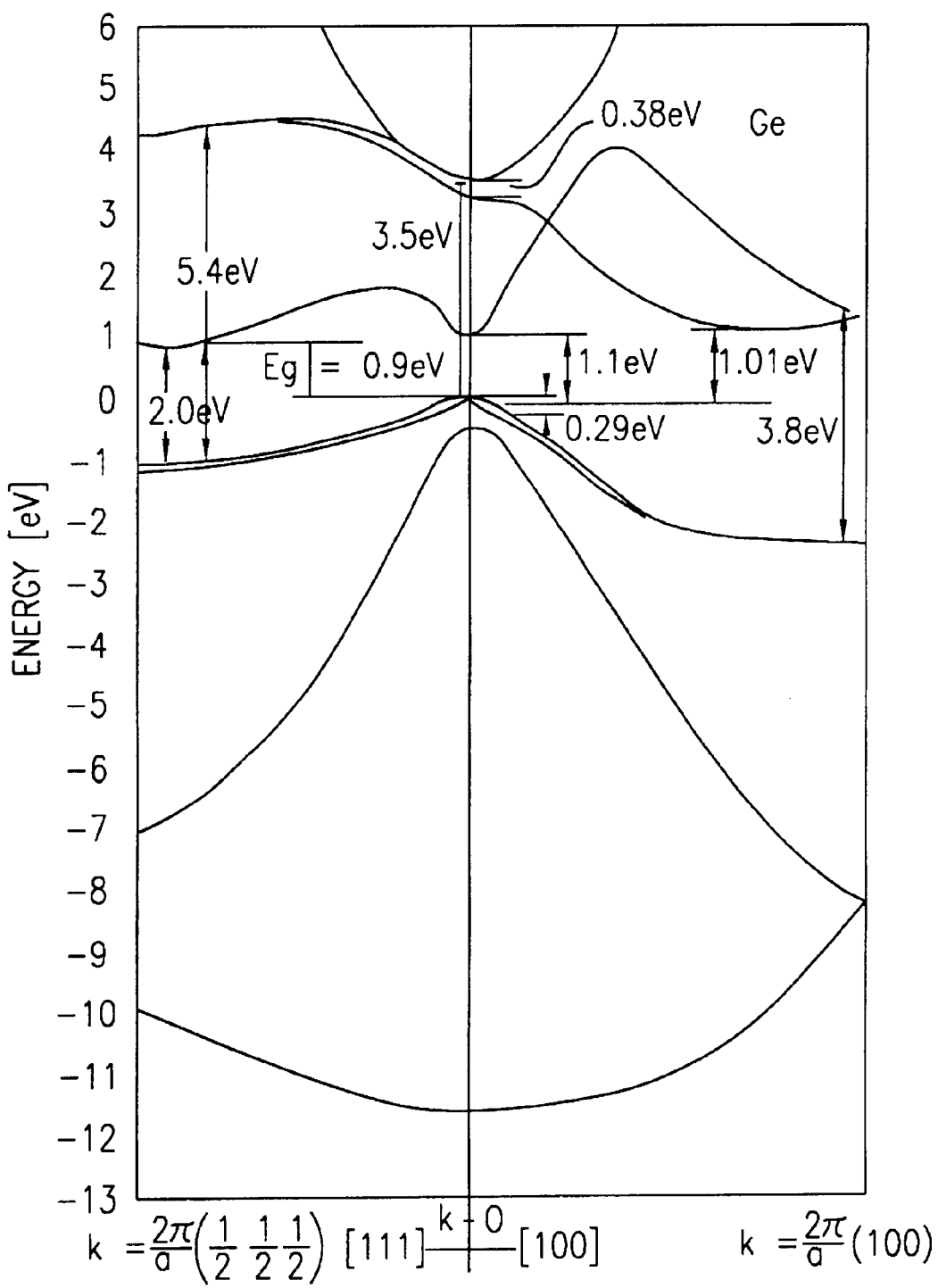
FIG. 2 is an energy band diagram for germanium (Ge) in which the energy is plotted with respect to the crystal momentum for two crystal directions.

FIG. 2 shows an energy band diagram for germanium (Ge) ("Introduction to Kittel's Solid-state Physics (first volume)," Maruzen, p. 211, 1982). As shown in this figure, since the photon energy of the fundamental wave of the Nd:YAG laser is greater than the bandgap energy near k=0, it is absorbed by the crystal, and through thermal motion, lattice vibrations occur. If a pulse oscillation laser is employed, the surface of the crystal can be irradiated with strong light can be in a moment. Therefore, a loss of energy due to thermal diffusion is small and the excitation of the lattice is easy. In this state, the p-polarized second harmonic with a photon energy of 2.3 eV is incident on the surface of the crystal. In that case, the photo energy of the second harmonic is greater than the bandgap energy 2 eV at k=2ρ/a (½ 1/2 1/2), so the probability of a second harmonic becomes high when the direction of polarization of the second harmonic matches the <111>-axis.

On the other hand, even when the direction of polarization of the second harmonic matches the <100>-axis, there is no transition caused by light of 2.3 eV and therefore there is no increase in the reflectance coefficient. Therefore, it can be judged by the computer 9 that the rotational angle at which the reflection ratio is maximum is the <111>-axis.

In the first embodiment of the present invention, while attention has been given to a transition of 2 ev and a description has been made of the reflectance coefficient of the light having a photo energy of more than 2 eV, it is a matter of course that similar advantages would be obtained even if attention was given to transitions other than that. In addition, lattice vibrations have been generated to measure a reflectance coefficient by a single laser in the first embodiment. However, it is a matter of course that, when two lasers or light sources were employed, there would be similar advantages.

SECOND EMBODIMENT

Figure 3:
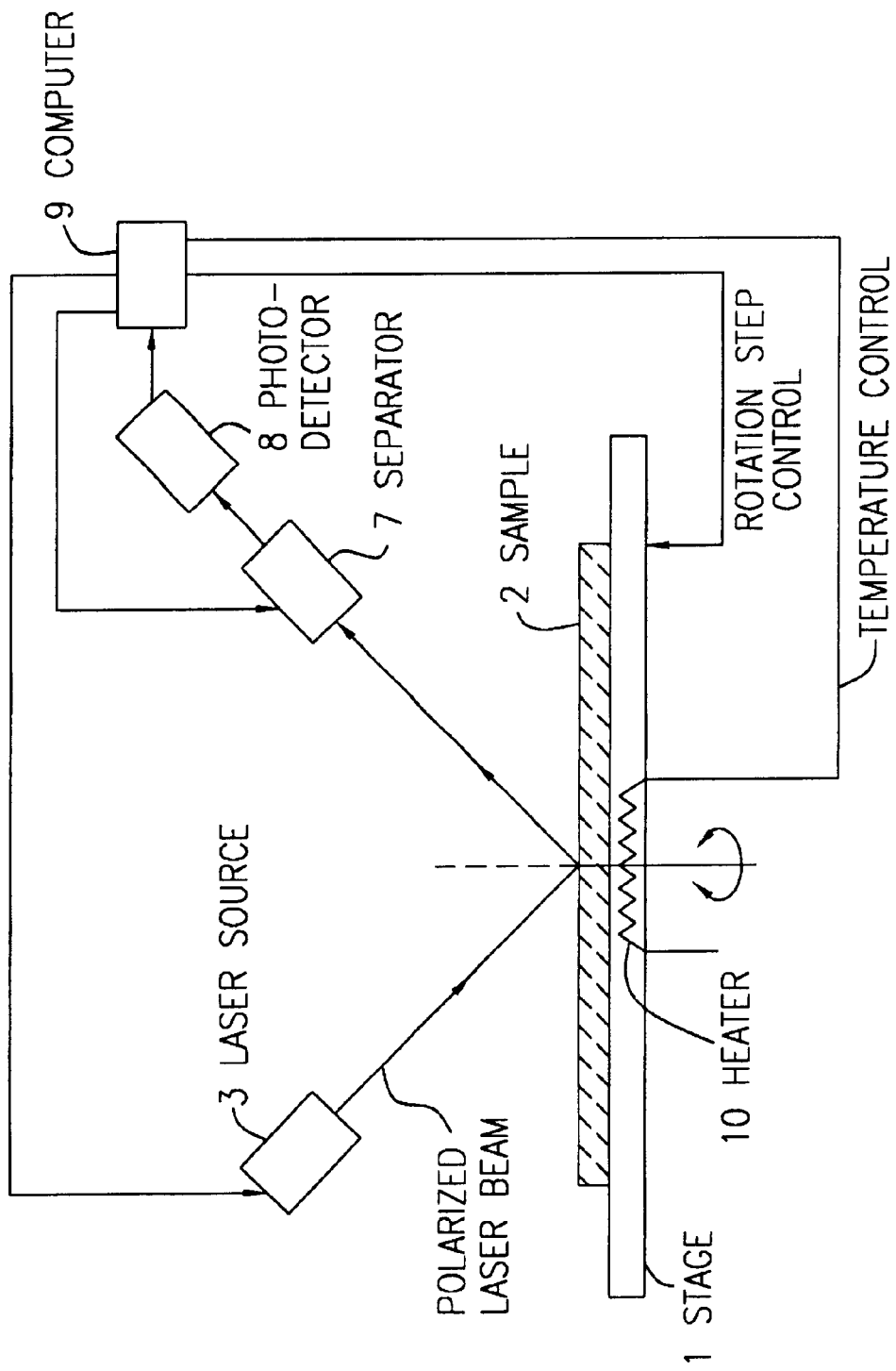
FIG. 3 is a schematic view showing an apparatus for measuring a crystal face orientation according to a second embodiment of the present invention.

Referring to FIG. 3, where elements similar to those previously described with reference to FIG. 1 are denoted by the same reference numerals, the stage 1 is provided with a heater 10 and is capable of rotating about the vertical axis in controlled angular steps. The sample 2 such as a crystal semiconductor is placed on the stage 1 and is irradiated with p-polarized laser beam while heated to a predetermined high temperature.

In this embodiment, the sample 2 employs germanium (Ge) having a (011)plane as its surface. The sample 2 on the stage 1 is heated to 900° C. by the heater 10. The sample 2 on the stage 1 is irradiated with p-polarized laser light of wavelength 620 nm emitted from the laser source 3 through a polarizer. The reflected light is transmitted through the separator 7 to filter out interfering light, and only the intensity of the reflected light is detected by the photodetector 8. The data of the intensity of the reflected light is stored onto the data memory of the computer 9.

Subsequently, the stage 1 is rotated by an angle of 0.1°, and in the same procedure as the aforementioned, the data of the intensity of the reflected light is stored. By repeating this process, the intensities of the reflected light are stored over 360°. The crystal lattice of the sample 2 is heated by the heater 63 and is vibrating due to its thermal motion. Therefore, as with the aforementioned embodiment, the reflectance coefficient becomes high only at the angle where the direction of polarization of the second harmonic included in the reflected light matches the <111>-axis.

In this embodiment, a semiconductor laser of wavelength 620 nm may be used as the laser source 3. Needless to say, similar advantages can also be obtained with a light source such as lamps and other lasers.

THIRD EMBODIMENT

Figure 4:
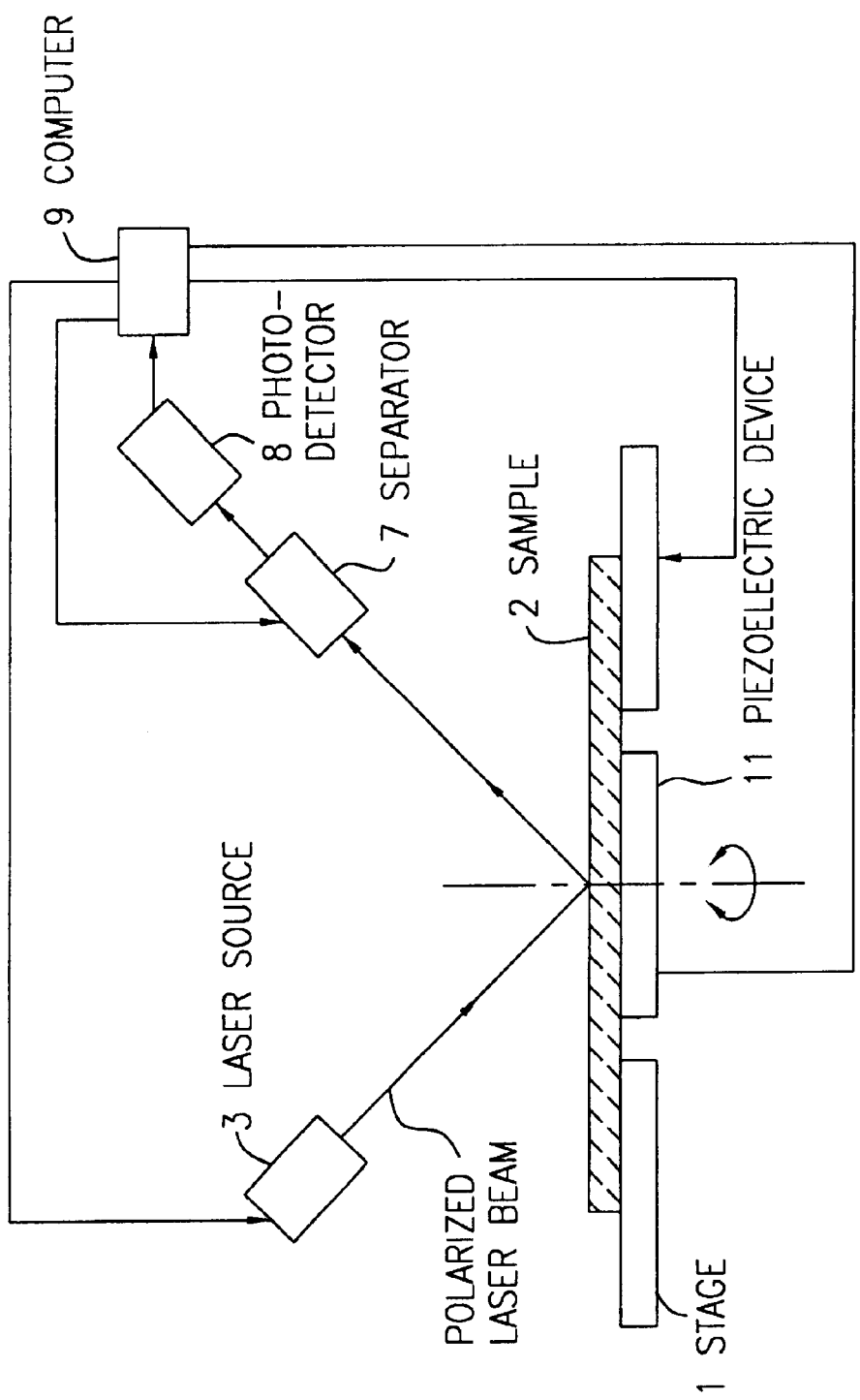
FIG. 4 is a schematic view showing an apparatus for measuring a crystal face orientation according to a third embodiment of the present invention.

Referring to FIG. 4, where elements similar to those previously described with reference to FIG. 1 are denoted by the same reference numerals, the sample 2 is placed on the stage 1 which is provided with a piezoelectric element 11. In this embodiment the sample 2 employs germanium (Ge) having a (011)-plane as its surface. The sample 2 on the stage 1 is given ultrasonic waves by the piezoelectric element 11 and is irradiated with p-polarized laser light of wavelength 620 nm emitted from the laser source 3 through a polarizer. The reflected light is transmitted through the separator 7 to filter out interfering light, and only the intensity of the reflected light is detected by the photodetector 8. The data of the intensity of the reflected light is stored onto the data memory of the computer 9.

Subsequently, the stage 1 is rotated by an angle of 0.1°, and in the same procedure as the aforementioned, the data of the intensity of the reflected light is stored. By repeating this process, the intensities of the reflected light are stored over 360°. The crystal lattice of the sample 2 is given ultrasonic waves during measurements by the piezoelectric element 11 and is vibrating due to its thermal motion. Therefore, the reflectance coefficient becomes high only at the angle where the direction of polarization of the second harmonic matches the <111>-axis. In the third embodiment shown in FIG. 4, while the piezoelectric element 11 has been embedded into the stage 1, the element does not always have to be embedded if it can supply ultrasonic waves to the sample sufficiently.

In this embodiment, a semiconductor laser of wavelength 620 nm may be used as the laser source 3. Needless to say, similar advantages can also be obtained with a light source such as lamps and other lasers.

Furthermore, in the aforementioned three embodiments, although the angular step is set to 0.1° and the rotational angle to 360°, in the required resolution range the angular step of the sample 2 may be selected in an arbitrary range so that the reflectance coefficient has a peak within the rotational angle.

FOURTH EMBODIMENT

Figure 5:
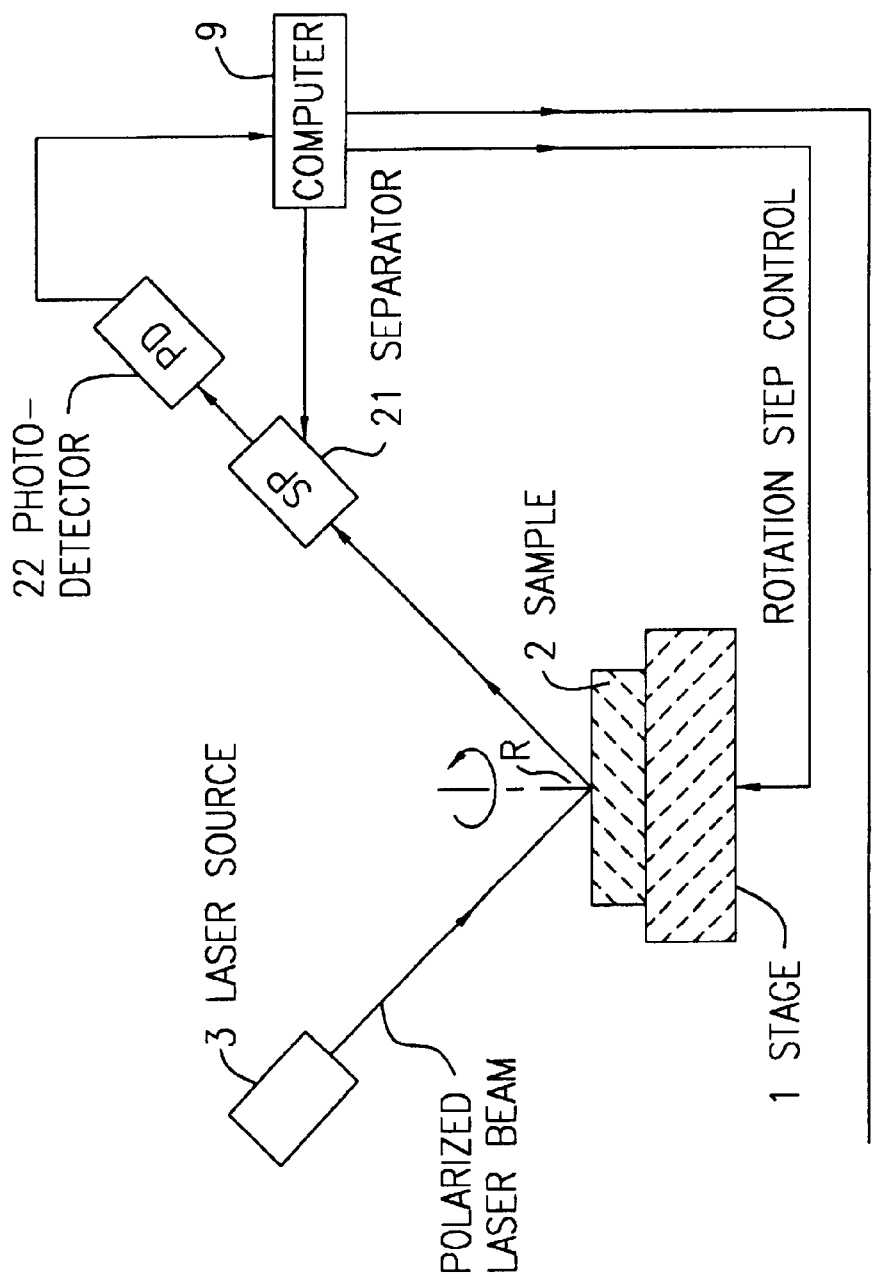
FIG. 5 is a schematic view showing an apparatus for measuring a crystal face orientation according to a fourth embodiment of the present invention.
Figure 6:
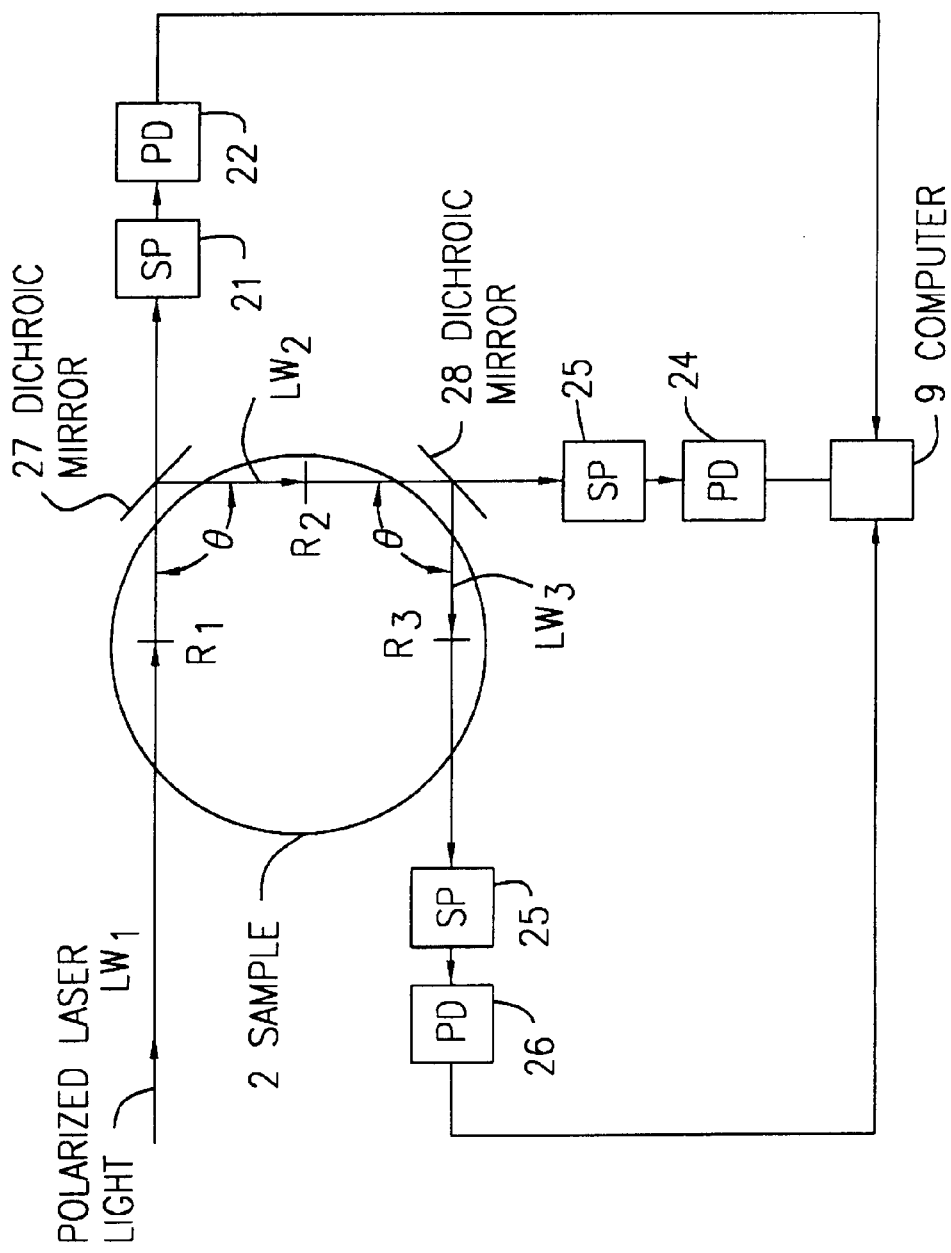
FIG. 6 is a schematic top view showing the apparatus as shown in FIG. 5.

Referring to FIGS. 5 and 6, where elements similar to those previously described with reference to FIG. 1 are denoted by the same reference numerals, the sample 2 such as a crystal semiconductor is placed on the stage 1 and is irradiated with a polarized laser light $LW_1$ which is produced by the laser source 3 and a polarizer (not shown).

The polarized laser light $LW_1$ is reflected at a first reflection position $R_1$ of the sample 2. The second harmonic component of the first reflected light passes through a dichroic mirror 27 to reach a separator 21 and then the intensity of the first reflected light is detected by a photodetector 22. The remaining of the first reflected light is reflected by the dichroic mirror 27 to produce polarized laser light $LW_2$ which is incident on the sample 2. The angle θ between the incident plane of the first reflected and the reflecting plane of the polarized laser light $LW_2$ is determined depending on the arrangement of atoms of the sample 2 as will be described later.

The polarized laser light $LW_2$ is reflected at a second reflection position $R_2$ of the sample 2. The second harmonic component of the second reflected light passes through a dichroic mirror 28 to reach a separator 23 and then the intensity of the second reflected light is detected by a photodetector 24. The remaining of the second reflected light is reflected by the dichroic mirror 28 to produce polarized laser light $LW_3$ with the angle θ between the incident plane of the second reflected light and the reflecting plane of the polarized laser light $LW_3$. The polarized laser light $LW_3$ is reflected at a third reflection position $R_3$ of the sample 2 and the third reflected light is transmitted to a separator 25 and then the intensity of the third reflected light is detected by a photodetector 26.

The computer 9 includes a processor, a program memory, a data memory and other necessary devices which are not shown in this figure. The computer 9 stores data of the intensity of each reflected light at each rotation angle while rotating the stage 1 in predetermined angular steps. Based on the stored data, the computer 9 calculates the peaks of the stored intensities to determine the crystal face orientation of the sample 2.

More specifically, a silicon substrate with a (100)-plane is used as the sample 2 and is placed on the stage 1. A pulse oscillation Nd:YAG laser of wavelength 1064 nm is employed as the laser source 3. The laser source 3 generates a laser beam which passes through a polarizer to produce the p-polarized light $LW_1$ consisting of a fundamental of wavelength 1064 nm. The position $R_1$ of the sample 2 is irradiated with the p-polarized light $LW_1$, having an arbitrary incident angle. As described before, when the p-polarized light $LW_1$ of wavelength 1064 nm is reflected by the crystal of the sample 2, a second harmonic of wavelength 532 nm is generated in the reflecting direction. Since the first reflected light including the second harmonic is emitted to the dichroic mirror 27, the first reflected light is divided into the polarized laser light of the fundamental and the second harmonic by the dichroic mirror 27. The second harmonic is transmitted through the separator 21 which completely filters out the fundamental laser light which will cause noise. The second harmonic from the separator 21 is detected as a first electric signal by the photodetector 22.

The remaining of the first reflected light changes its traveling direction by the angle θ (here 90°) relative to the original traveling direction to produce the polarized laser light $LW_2$. The angle θ is determined depending on the arrangement of atoms of the sample 2 as will be described later. In the case of Si(100), the angle θ is set to 90°.

Similarly, the polarized laser light $LW_2$ is reflected at the second reflection position $R_2$ of the sample 2 and the intensity of the second harmonic component is detected by the photodetector 24. The remaining of the second reflected light is reflected by the dichroic mirror 28 to change its traveling direction by the angle θ (here 90°) relative to the original traveling direction to produce the polarized laser light $LW_3$. After reflected at the third reflection position $R_3$, the intensity of the second harmonic is detected by the photodetector 26.

The aforementioned first, second, and third detected signals are stored on the computer 9 along with each rotational angle relative to an axis perpendicular to the surface of the sample 2 on the stage 1.

Figure 11:
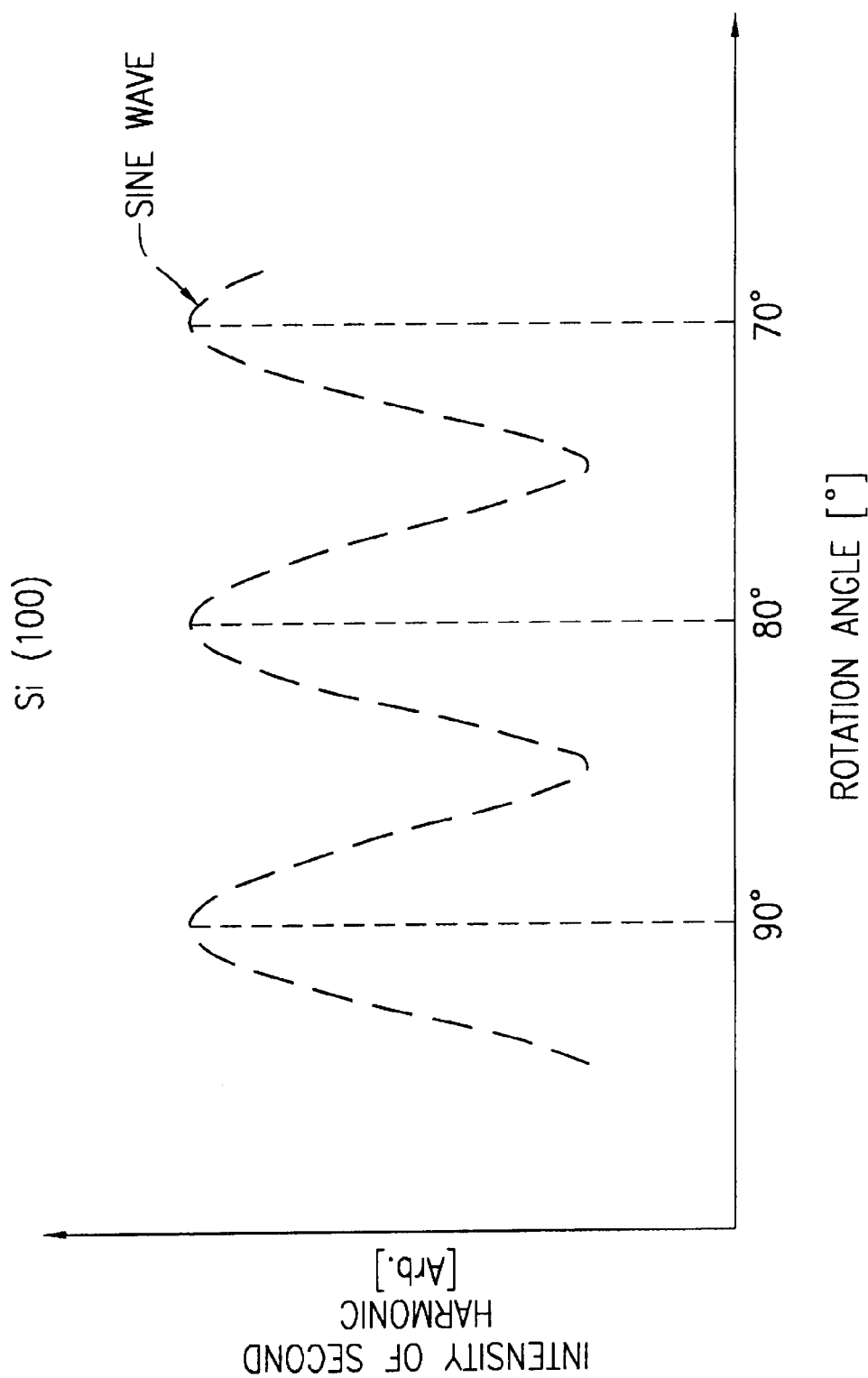
FIG. 11 is a schematic diagram showing a change of the intensity of second harmonic with respect to the rotational angle of a sample.

Next, the stage 1 is rotated by an angle of 0.1°, and in the aforementioned same procedure, the intensity of the second harmonic is detected. By repeating this cycle, the intensities of the second harmonic are measured over 360°. The intensity of the second harmonic varies like a sine wave with respect of the rotational angle of the stage 1 (see FIG. 11). This sine wave becomes maximum when the direction of polarization of laser light matches the direction of a line linking corner atoms on the (100)-plane of the diamond lattice structure of silicon. Therefore, the maximum and the minimum in the intensity alternately occurs in intervals of 90°.

By using this, it will be found that, at the angle which exhibits the maximum intensity, the traveling direction of the laser light projected perpendicularly on the sample surface will indicate the <001>-direction, and consequently, the crystal orientation can be determined. Furthermore, it is obvious that the arrangement of atoms determines the traveling direction of the fundamental. During measurements, the computer 9 performs the determination of the crystal face orientation based on the rotational angle dependency of the intensities of the second harmonic. Needless to say, the computer 9 may control the laser source 3 so as to keep the intensity of the laser beam constant, resulting in improved reliability and more precise measurement.

Furthermore, after the measurement, the stage 1 is rotated to the angle which exhibits the maximum intensity, and the positions of the separators end the photodetectors are moved from those of the mirror reflection of laser light. Then, a groove is formed on the sample 2 by abrasion caused by raising the intensity of the laser light and scanning the laser light on the incident and reflecting plane. At this time, the scanning direction of the laser light corresponds to the <001>-axis of silicon. Therefore, the groove formed by abrasion can be used as the orientation flat which is used in current semiconductor wafers.

In the fourth embodiment, the case of the (100)-crystal plane of silicon has been described as an example. Measurement can also be made in the same way for the case of the (111)-plane of silicon. However, in the case of the (111)-plane of silicon, the intensity of the second harmonic against a rotational angle exhibits one cycle at 60°, so it is necessary to set the angle to θ to 60°.

FIFTH EMBODIMENT

Figure 7:
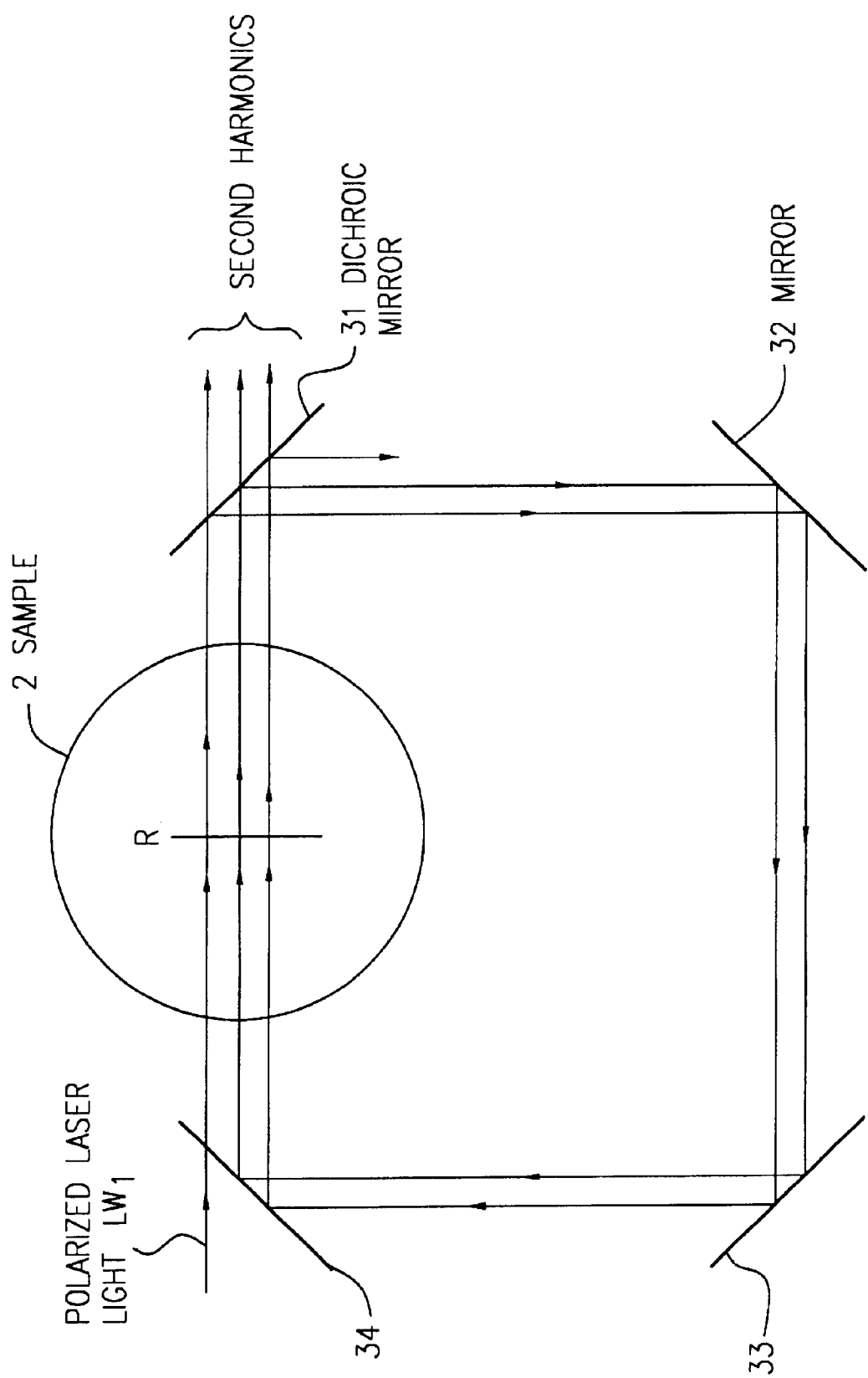
FIG. 7 is a schematic top view showing an apparatus for measuring a crystal face orientation according to a fifth embodiment of the present invention.

Referring to FIG. 7, where elements similar to those previously described with reference to FIG. 5 are denoted by the same reference numerals, the sample 2 placed on the stage 1 is irradiated with the p-polarized laser light $LW_1$. The reflected light includes the fundamental of the laser light $LW_1$ and a second harmonic generated on the sample 2. The second harmonic is transmitted through a dichroic mirror 31, while the fundamental is reflected and directed to a first mirror 32. The fundamental is reflected by the first mirror 32 and is directed to a second mirror 33. Likewise, the fundamental is reflected by the second mirror 33 and is directed to a third mirror 34. The fundamental reflected by the third mirror 34 is incident on the sample 2 again. At this time, the direction of the fundamental reflected by the third mirror 34 is parallel to that of the first laser light $LW_1$. Thus, only the generated second harmonic is transmitted through the dichroic mirror 31 and advances to a separator (not shown). On the other hand, the fundamental repeats the aforementioned cycle and is confined within the four mirrors 31–34. Therefore, the second harmonic is generated efficiently. In this arrangement, the laser light $LW_1$ can be easily in phase with the second harmonic by adjusting the positions of the dichroic mirror 40 and the three mirrors 32–34.

The intensity of the second harmonic is measured and the corresponding rotational angle are stored on the computer 9. Subsequently, the stage 1 is rotated by an angle of 1°. By repeating this operation, the crystal face orientation of the sample 2 can be detected in the same method as the first embodiment shown in FIG. 1.

In the fifth embodiment of FIG. 7., while an example of the resonator using a single dichroic mirror 31 and three mirrors 32–34 has been shown, it is a matter of course that the same advantage is obtained even when the number of mirrors is changed to constitute the resonator.

SIXTH EMBODIMENT

For simplicity, the basic structure of the apparatus will be described with a similar example as FIG. 5. In this embodiment, an irradiation system and a light receiving system are different. The top view of the irradiation and light receiving systems is shown in FIG. 8.

Figure 8:
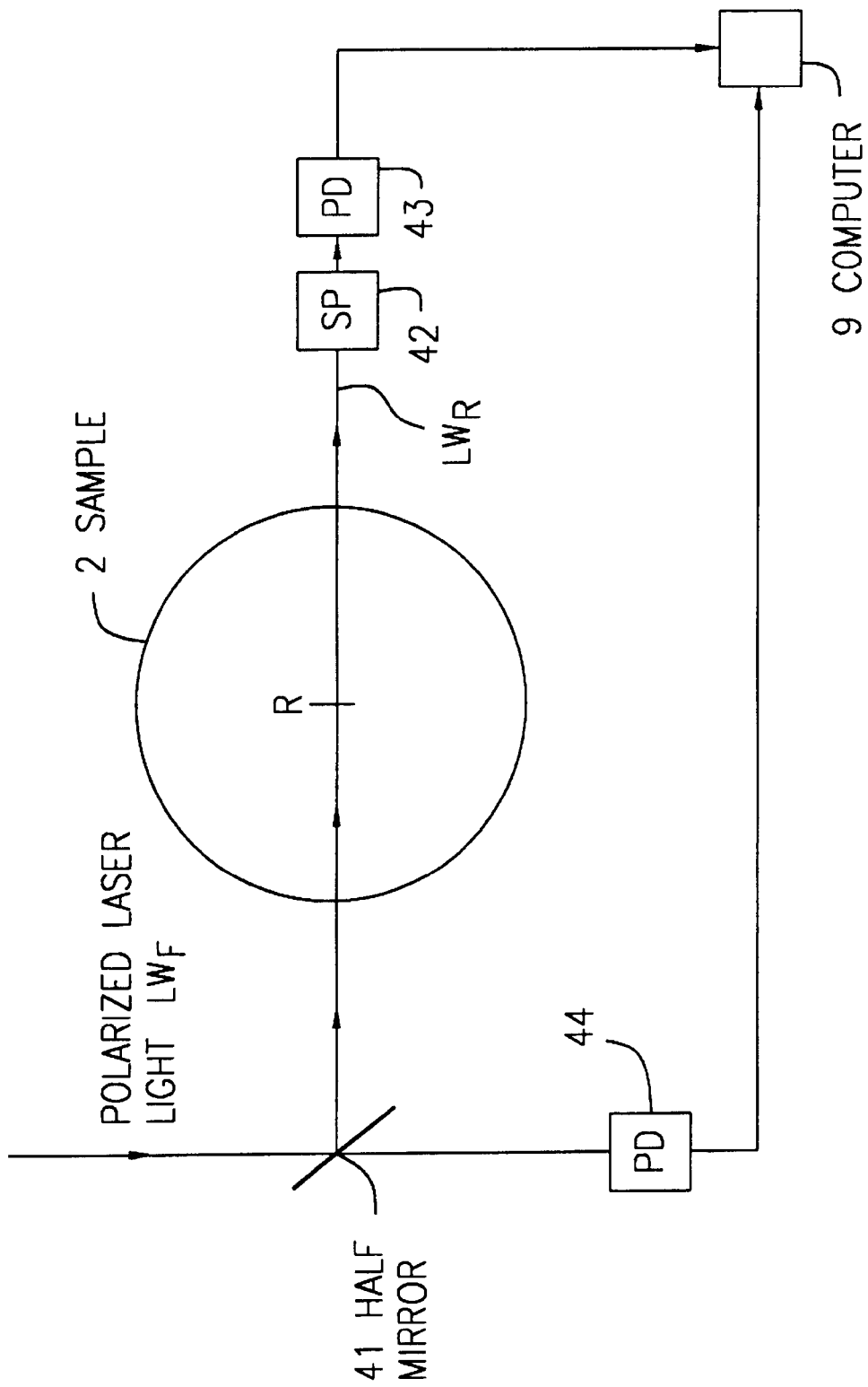
FIG. 8 is a schematic top view showing an apparatus for measuring a crystal face orientation according to a sixth embodiment of the present invention.

Referring to FIG. 8, where elements similar to those previously described with reference to FIG. 5 are denoted by the same reference numerals, the polarized laser light $LW_F$, emitted from the laser source 3, is divided into two light beams by a half mirror 41, and one of the light beams is incident on the sample 2. The second harmonic generated from the sample is transmitted through a separator 42 and the intensity thereof is detected by a photodetector 43. The other of the beams divided by the half mirror 41 is transmitted through a photodetector 44 which detects the intensity thereof. The detection signals of the fundamental and the second harmonic are output to the computer 9. The intensity of the second harmonic is proportional to the square of that of the fundamental. Therefore, the intensity of the detected second harmonic can be normalized by the square of the intensity of the detected fundamental. This causes a fluctuation in the intensity of the incident laser light $LW_F$ to be canceled out, resulting in that the signal-to-noise ratio can be about 10 times enhanced and the second harmonic can be measured with a high degree of accuracy.

Thereafter, while rotating the stage in steps, the intensity of the second harmonic is detected at each angular step in the aforementioned way. Therefore, the crystal face orientation of the sample can be obtained in the same way as the first embodiment.

SEVENTH EMBODIMENT

For simplicity, the basic structure of the apparatus will be described with a similar example as FIG. 5. In this embodiment, the irradiation system and the light receiving system are different. The top view of the irradiation and light receiving systems is shown in FIG. 9.

Figure 9:
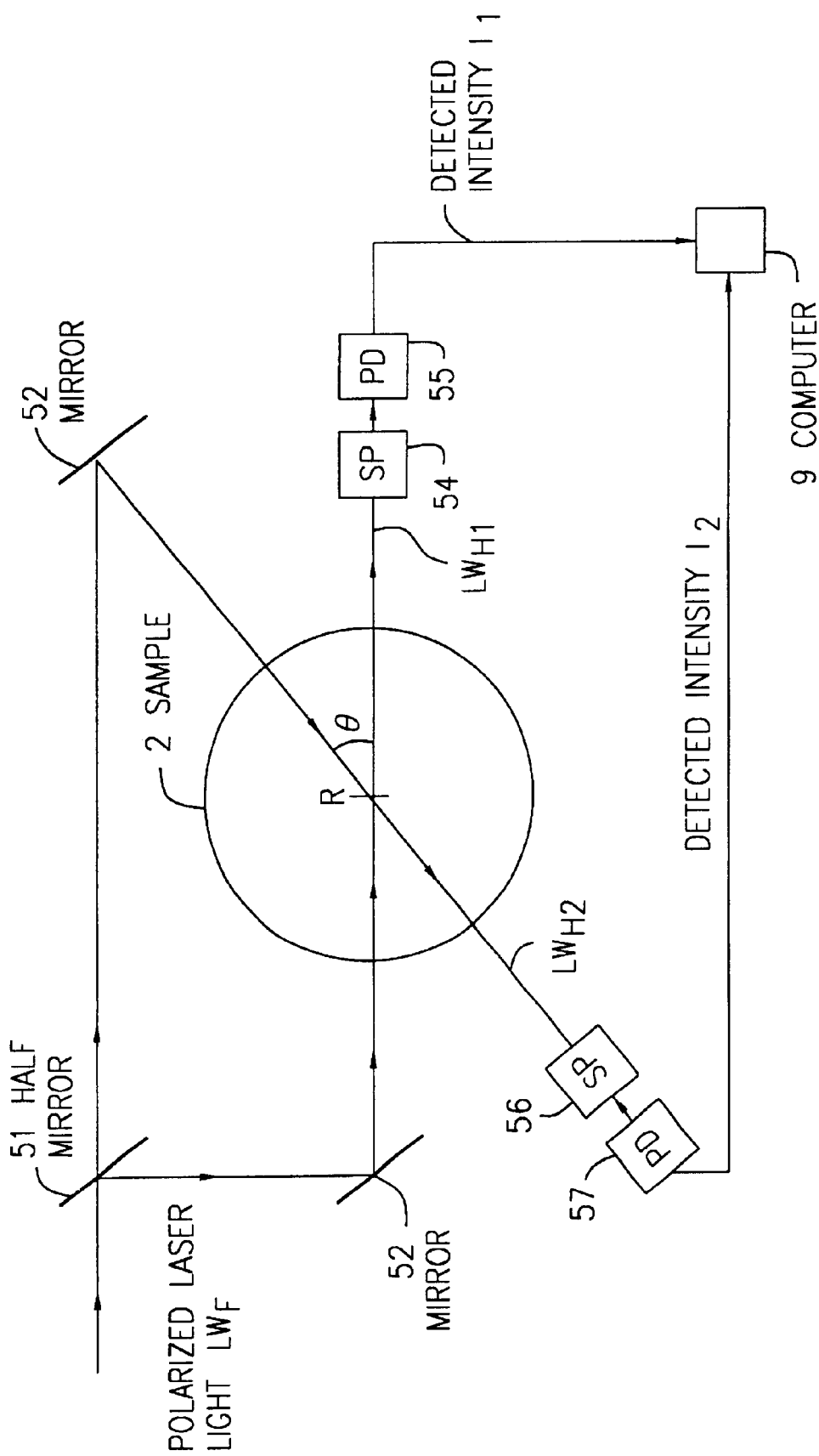
FIG. 9 is a schematic top view showing an apparatus for measuring a crystal face orientation according to a seventh embodiment of the present invention.

Referring to FIG. 9, the polarized laser light $LW_F$ which is emitted from the laser source 3 is divided into two light beams by a half mirror 51. The two light beams are reflected by first and second mirrors 52 and 53, respectively, and the sample 2 is irradiated with the respective reflected light beams. In the case of the sample 2 being silicon (Si) with a face orientation of (100), the incident planes of the two light beams will cross each other at an angle θ of 45°. On the (100)-plane of silicon, the intensity of a second harmonic varies like a sine wave with a rotational angle of 90° as one cycle, so the respective second harmonics generated by the two light beams are shifted in phase by exactly a half cycle.

By irradiating the sample 2 with the two light beams, two harmonics $LW_{H1}$ and $LW_{H2}$ are generated and travel in the same directions as the two light beams, respectively. The first harmonic $LW_{H1}$ is transmitted through a first separator 54 and its intensity $I_1$ is detected by a first photodetector 55. Similarly, the second harmonic $LW_{H2}$ is transmitted through a second separator 56 and its intensity $I_2$ is detected by a second photodetector 57. The detected intensity signals $I_1$ and $I_2$ are transmitted to the computer 9 and are stored onto the data memory.

Subsequently, the stage 1 is rotated and measurements are repeated in the same way as the above embodiments. In this embodiment, the computer 9 calculates the ratio of the intensities $I_1$ and $I_2$ of the second harmonics $LW_{H1}$ and $LW_{H2}$ that is, $I_1-I_2$, for each rotational angle. Alternatively, these intensities $I_1$ and $I_2$ are adjusted in level to have the same level before the difference between them is calculated, that is, $I_1-I_2$, for each rotational angle. With calculations like these, noises in the same phase which are included in the second harmonics $LW_{H1}$ and $LW_{H2}$ are canceled, and consequently, the signal-to-noise ratio can be about 10 times improved and a high-precise measurement of face orientation can be achieved.

EIGHTH EMBODIMENT

This embodiment is a modification of the seventh embodiment as shown in FIG. 9 and is an example of the case where a single laser light beam is employed. The top view of the irradiation and light receiving systems is shown in FIG. 10.

Figure 10:
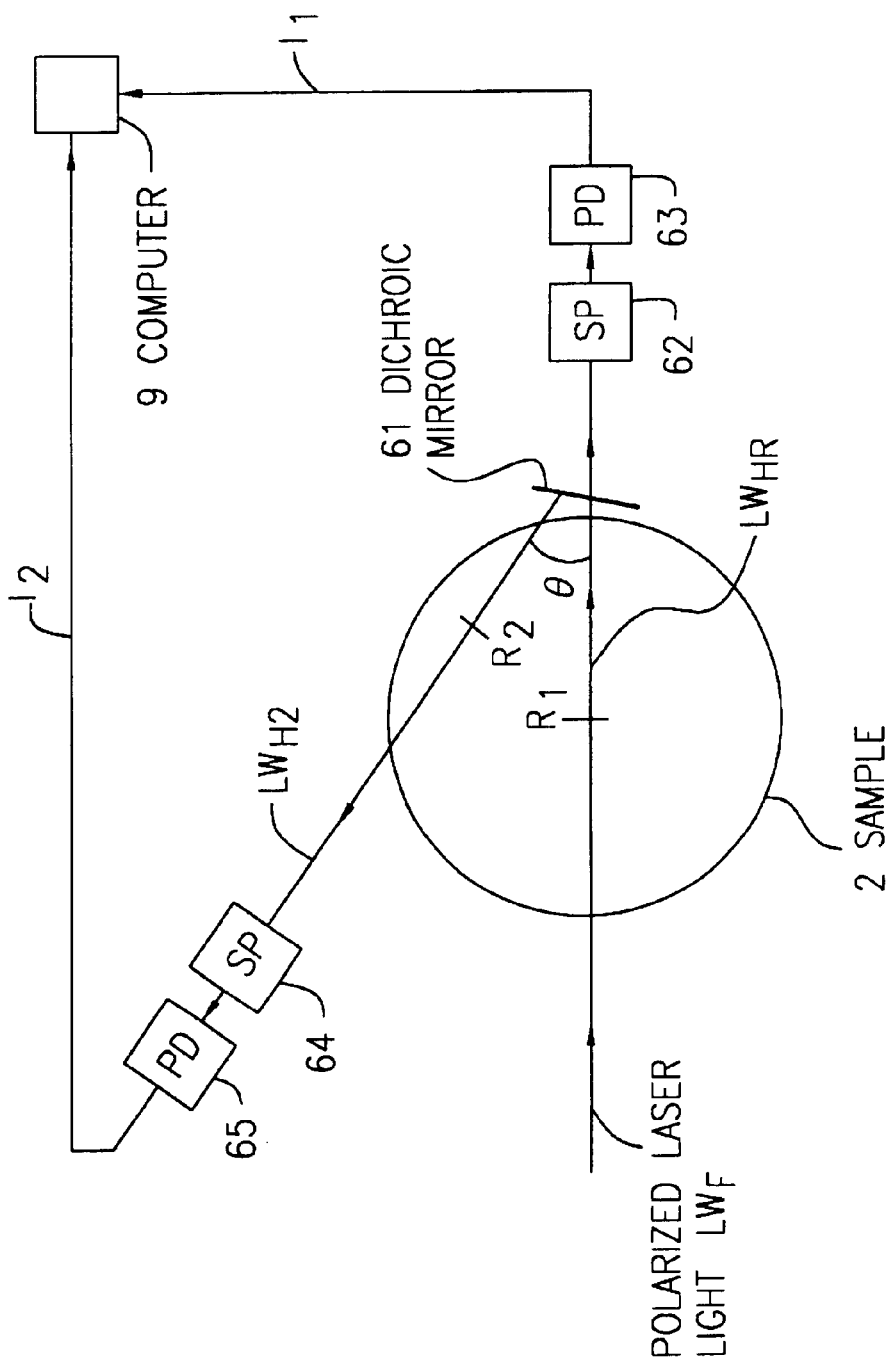
FIG. 10 is a schematic top view showing an apparatus for measuring a crystal face orientation according to an eighth embodiment of the present invention.

Referring to FIG. 10, a first position $R_1$ of the sample 2 placed on the stage 1 is irradiated with the polarized laser light $LW_F$ which is generated by the laser source 3. The reflected light includes a fundamental $LW_{H1}$ and a second harmonic $LW_{H2}$ which is generated on the sample 2. The first harmonic $LW_{H1}$ is transmitted through both a dichroic mirror 61 and a first separator 62 and its intensity $I_1$ is detected by a first photodetector 63. On the other hand, the fundamental of the reflected light is reflected by the dichroic mirror 61 and another position $R_2$ of the sample 2 is irradiated with the reflected fundamental again. This causes a second harmonic $LW_{H2}$ to be generated on the sample 2. The second harmonic $LW_{H2}$ is transmitted through a second separator 64 and its intensity $I_2$ is detected by a second photodetector 65.

In the case of the sample 2 being silicon (Si) with a face orientation of 100), the reflecting plane of the second harmonic $LW_H$ will cross the incident plane of the reflected fundamental with respect to the surface of the sample 2 at an angle θ of 45°. On the (100)-plane of silicon, as previously described, the intensities $I_1$ and $I_2$ of the respective harmonics $LW_{H1}$ and $LW_{H2}$ are shifted by exactly a half cycle. The signals detected by the first and second photodetectors 63 and 65 are transmitted to the computer 9 and are stored onto the data memory.

The stage 1 having the sample 2 placed thereon is rotated and measurements are repeated in the same way as the above embodiment. In this embodiment, the computer 9 calculates the ratio of the intensity $I_1$ of the first harmonic $LW_{H1}$ to the intensity 12 of the second harmonics $LW_{H2}$ having a weight $\alpha^2$, that is, $I_1/\alpha^2 I_2$, for each rotational angle. Alternatively, these intensities $I_1$ and $\alpha^2 I_2$ are adjusted in level to have the same level before the difference between them is calculated, that is, $I_1-\alpha^2 I_2$ for each rotational angle. Here, α represents a ratio of the intensity of laser light obtained when it is first irradiated on a sample and the intensity of laser light obtained after it is reflected by the dichroic mirror 61. With computations like these, the noises in the same phase which are included in the second harmonics $LW_{H1}$ and $LW_{H2}$ are canceled, and consequently, the signal-to-noise ratio can be considerably enhanced and a high-precise measurement of surface orientation becomes possible. In the seventh and eighth embodiments as shown in FIGS. 9 and 10, the angle θ is determined so that the respective intensity variations of the two second harmonics $LW_{H1}$ and $LW_{H2}$ differ in phase by a half cycle. More specifically, assuming that the order of the symmetry of rotation of a certain crystal is N, an angle of (360/2N)·(2M+1), where M is an integer, will cause the phase of intensity variation of the second harmonic to be shifted by exactly a half cycle.

In the first to eighth embodiments as described above, while the second harmonic has been employed as an example, it is a matter of course that the same advantages are also obtainable for the case of Raman light if it is normalized by one power of laser light intensity. Further, in the embodiments, it is a matter of course that there are the same advantages even when the rotational angle dependency of the intensity of reflected light other than a second harmonic is measured. In addition, in that case, there are the same advantages even when a light source such as a lamp is employed instead of a laser device.

Furthermore, in the embodiments aforementioned, while the rotational step and angle have been 1° and 360°, respectively, they may be set arbitrarily in accordance with the rotational angle dependency of the second harmonic of a sample to be measured. Needless to say, there are the same advantages when the irradiation system and the light receiving system are rotated with respect to a sample instead of rotating the sample.

The separators used in the above embodiments may be comprised of a combination of a filter and an analyzer. The photodetectors may be comprised of a photomultiplier or a photodiode.

It is apparent that a combination of a means of exciting the crystal lattice of the sample and each of the fourth to eighth embodiments further improves the signal-to-noise ratio.

Although Group IV semiconductors such as silicon and germanium have been used as samples in the above embodiments, needless to say that the present invention can be applied to any crystal material, for example, Group III-V compound semiconductors such as GaAs and InP as well as II-VI compound semiconductors.

While the invention has been described with reference to preferred embodiments thereof, the invention is not to be limited to the details given herein, but may be modified within the scope of the appended claims.

What is claimed is:

1. A method for determining a crystal face orientation of a crystal sample, the method comprising:
    rotating the sample about an axis perpendicular to a surface of the sample;
    irradiating the surface of the sample with first incident light;
    reflecting the first incident light off of the surface of the sample thereby producing first reflected light;
    reflecting at least a portion of the first reflected light back on to the surface of the sample, the portion being second incident light;
    reflecting the second incident light off of the surface of the sample thereby producing second reflected light;
    detecting a first reflected intensity of the energy of the first reflected light;
    detecting a second reflected intensity of the energy of the second reflected light; and
    determining the crystal face orientation of the sample based on the first and second reflected intensities.

2. The method as recited in claim 1, wherein the first incident light is produced by laser.

3. The method as recited in claim 1, wherein the first reflected intensity includes the second harmonic of the first incident light.

4. The method as recited in claim 1, wherein the second reflected intensity includes the second harmonic of the second incident light.

5. The method as recited in claim 1, wherein the first incident light is produced by a laser.

6. The method as recited in claim 1, wherein the first incident light has a wavelength of approximately 1064 nm.

7. The method as recited in claim 1, wherein the first incident light includes p-polarized light.

8. The method as recited in claim 1, wherein the first incident light includes polarized light.

9. The method as recited in claim 1, wherein the rotating includes rotating the sample in angular steps.

10. The method as recited in claim 1, wherein the reflecting at least a portion of the first reflected light is performed by a dichroic mirror.

11. An apparatus for determining a crystal face orientation of a crystal sample, the apparatus comprising:
    a stage which is effective to rotate the sample about an axis perpendicular to a surface of the sample;
    a light source disposed so that it is effective to irradiate the surface of the sample with first incident light, the first incident light reflecting off of the surface of the sample and producing first reflected light;
    a first detector which detects a first reflected intensity of the energy of the first reflected light;
    a reflector which reflects at least a portion of the first reflected light back to the surface of the sample, the portion being second incident light, the second incident light reflecting off of the surface of the sample and producing second reflected light;
    a second detector disposed so that it detects a second reflected intensity of the energy of the second reflected light; and
    a processor, coupled to the first and second detectors, the processor determines the crystal face orientation of the sample based on the first and second reflected intensity.

12. The apparatus as recited in claim 11, wherein the light source is produced by a laser.

13. The apparatus as recited in claim 11, wherein the first reflected intensity includes the second harmonic of the first incident light.

14. The apparatus as recited in claim 11, wherein the second reflected intensity includes the second harmonic of the second incident light.

15. The apparatus as recited in claim 11, wherein the first incident light includes light produced by a laser.

16. The apparatus as recited in claim 11, herein the first incident light has a wavelength of approximately 1064 nm.

17. The apparatus as recited in claim 11, wherein the first incident light includes p-polarized light.

18. The apparatus as recited in claim 11, wherein the first incident light includes polarized light.

19. The apparatus as recited in claim 11, wherein the stage rotates the sample in angular steps.

20. The apparatus as recited in claim 11, wherein the reflector includes a dichroic mirror.

21. A method for determining a crystal face orientation of a crystal sample, the method comprising:
    rotating the sample about an axis perpendicular to a surface of the sample;
    irradiating the surface of the sample with incident light;
    reflecting the incident light off of the surface of the sample thereby producing reflected light;
    detecting a reflected intensity of the energy of a first portion of the reflected light;
    continually reflecting a second portion of the reflected light back toward the surface of the sample; and
    determining the crystal face orientation of the sample based on the reflected intensity.

22. The method as recited in claim 21, wherein the first portion of the reflected light includes a second harmonic of the incident light and the second portion of the reflected light includes a first harmonic of the incident light.

23. The method as recited in claim 21, wherein the light source is produced by a laser.

24. The method as recited in claim 21, wherein the first incident light includes p-polarized light.

25. The method as recited in claim 21, wherein the first incident light includes polarized light.

26. The method as recited in claim 21, wherein the rotating includes rotating the sample in angular steps.

27. The method as recited in claim 21, wherein the continually reflecting a second portion of the reflected light is performed by a dichroic mirror.

28. The method as recited in claim 21, wherein the continually reflecting a second portion of the reflected light is performed by a plurality of dichroic mirrors.

29. An apparatus for determining a crystal face orientation of a crystal sample, the apparatus comprising:
   a stage which is effective to rotate the sample about an axis perpendicular to a surface of the sample;
   a light source disposed so that it is effective to irradiate the surface of the sample with incident light, the incident light reflecting off of the surface of the sample thereby producing reflected light;
   a detector which detects a reflected intensity of the energy of a first portion of the reflected light;
   a reflector effective to continually reflect a second portion of the reflected light back toward the surface of the sample; and
   a processor, coupled to the detector, the processor effective to determine the crystal face orientation of the sample based on the reflected intensity.

30. The apparatus as recited in claim 29, wherein the first portion of the reflected light includes a second harmonic of the incident light and the second portion of the reflected light includes a first harmonic of the incident light.

31. The apparatus as recited in claim 29, wherein the light source includes a laser.

32. The apparatus as recited in claim 29, herein the first incident light includes p-polarized light.

33. The apparatus as recited in claim 29, wherein the first incident light includes polarized light.

34. The apparatus as recited in claim 29, wherein the stage rotates the sample in angular steps.

35. The apparatus as recited in claim 29, wherein the reflector comprises at least one dichroic mirror.

36. The apparatus as recited in claim 29, wherein the reflector comprises 4 dichroic mirrors.

37. A method for determining a crystal face orientation of a crystal sample, the method comprising:
   rotating the sample about an axis perpendicular to a surface of the sample;
   irradiating a first location on the surface of the sample with an initial light;
   reflecting the initial light off of the surface of the sample thereby producing a first reflected light;
   detecting a first reflected intensity of the energy of the first reflected light;
   reflecting a portion of the first reflected light back on to the surface of the sample at a second location on the sample, the second location being distinct from the first location;
   reflecting the portion of the first reflected light off of the sample thereby producing a second reflected light;
   detecting a second reflected intensity of the energy of the second reflected light; and
   determining the crystal face orientation of the sample based on the first and second reflected intensity.

38. The method as recited in claim 37, wherein the initial light is produced by a laser.

39. The method as recited in claim 37, wherein:
   the first reflected light includes a second harmonic of the initial light; and
   the detecting a first reflected intensity includes detecting the second harmonic of the initial light.

40. The method as recited in claim 37, wherein:
   the second reflected light includes a second harmonic of the first reflected light; and
   the detecting a second reflected intensity includes detecting the second harmonic of the first reflected light.

41. The method as recited in claim 37, wherein the rotating includes rotating in angular steps.

42. An apparatus for determining a crystal face orientation of a crystal sample, the apparatus comprising:
   a stage which is effective to rotate the sample about an axis perpendicular to a surface of the sample;
   a light source disposed so that it is effective to irradiate a first location on the surface of the sample with an initial light, the initial light reflecting off of the surface of the sample thereby producing a first reflected light;
   a first detector which detects a first reflected intensity of the energy of a first portion of the first reflected light;
   a reflector which reflects a second portion of the first reflected light back on to the sample at a second location on the sample, the second location being distinct from the first location, the second portion reflecting off of the surface of the sample thereby producing a second reflected light;
   a second detector which detects a second reflected intensity of the energy of the second reflected light; and
   a processor coupled to the first and second detectors, the processor effective to determine the crystal face orientation of the sample based on the first and second reflected intensity.

43. The apparatus as recited in claim 42, wherein the initial light is produced by a laser.

44. The apparatus as recited in claim 42, wherein:
   the first reflected light includes a second harmonic of the initial light; and
   the first detector detects the second harmonic of the initial light.

45. The apparatus as recited in claim 42, wherein:
   the second reflected light includes a second harmonic of the first reflected light; and
   the second detector detects the second harmonic of the first reflected light.

46. The apparatus as recited in claim 42, wherein the stage rotates the sample in angular steps.

* * * * *